(12) United States Patent
Zhang

(10) Patent No.: US 11,471,472 B2
(45) Date of Patent: Oct. 18, 2022

(54) USE OF VERBASCOSIDE IN PREPARATION OF DRUG FOR PREVENTING OR TREATING GLOMERULAR PODOCYTE INJURED RENAL DISEASE

(71) Applicant: SICHUAN MEDCO PHARMACEUTICAL STOCK CO., LTD., Sichuan (CN)

(72) Inventor: Xiaoqi Zhang, Sichuan (CN)

(73) Assignee: SICHUAN MEDCO PHARMACEUTICAL STOCK CO., LTD., Sichuan (CN)

( * ) Notice: Subject to any disclaimer, the term of this patent is extended or adjusted under 35 U.S.C. 154(b) by 0 days.

(21) Appl. No.: 16/643,969

(22) PCT Filed: Oct. 13, 2017

(86) PCT No.: PCT/CN2017/106171
§ 371 (c)(1),
(2) Date: Mar. 3, 2020

(87) PCT Pub. No.: WO2019/041467
PCT Pub. Date: Mar. 7, 2019

(65) Prior Publication Data
US 2021/0060046 A1 Mar. 4, 2021

(30) Foreign Application Priority Data
Sep. 4, 2017 (CN) .......................... 201710783928.5

(51) Int. Cl.
*A61K 31/7034* (2006.01)
*A61P 13/12* (2006.01)
*A61K 47/10* (2017.01)
*A61K 47/32* (2006.01)
*A61K 47/38* (2006.01)

(52) U.S. Cl.
CPC .......... *A61K 31/7034* (2013.01); *A61P 13/12* (2018.01); *A61K 47/10* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 2005/0123543 A1* | 6/2005 | Kretzler | C07K 16/40 424/146.1 |
| 2008/0255181 A1* | 10/2008 | Oh | A61P 13/12 514/297 |
| 2012/0053174 A1* | 3/2012 | Hadd | C07D 405/14 514/230.8 |
| 2014/0026917 A1* | 1/2014 | Monteiro | A61K 8/463 132/205 |

FOREIGN PATENT DOCUMENTS

| | | | |
|---|---|---|---|
| CN | 101121740 A | 2/2008 | |
| CN | 107375308 A | 11/2017 | |
| JP | 2013023478 A | * 2/2013 | ......... A61K 31/7034 |
| JP | 5969738 B2 | 8/2016 | |

OTHER PUBLICATIONS

Hayashi, K., Nagamatsu, T., Ito, M., Yagita, H., & Suzuki, Y. (1996). Acteoside, a component of Stachys sieboldii MIQ, maybe a promising antinephritic agent (3): effect of acteoside on expression of intercellular adhesion molecule-11 . . . The Japanese journal of pharmacology, 70(2), 157-168. (Year: 1996).*
Coers, W., Brouwer, L., Vos, J. T. W. M., Chand, A., Huitema, S., Heeringa, P., . . . & Weening, J. J. (1994). Podocyte expression of MHC class I and II and intercellular adhesion molecule-1 (ICAM-1) in experimental. Clinical & Experimental Immunology, 98(2), 279 (Year: 1994).*
Dai, X. X., Su, S. L., Cai, H. D., Wei, D. D., Zheng, T. Y., Zhu, Z. H., . . . & Duan, J. A. (2017). Comparative pharmacokinetics of acteoside from total glycoside extracted from leaves of Rehmannia and Dihuangye to. Biomedical Chromatography, 31(12), e4013. (Year: 2017).*
Canton, A., Fuiano, G., Sepe, V., Caglioti, A., & Ferrone, S. (1992). Mesangial expression of intercellular adhesion molecule-1 in primary glomerulosclerosis. Kidney international, 41(4), 951-955. (Year: 1992).*
D'agati, V. D. (2008). Podocyte injury in focal segmental glomerulosclerosis: Lessons from animal models (a play in five acts). Kidney international, 73(4), 399-406. (Year: 2008).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Ding, F., Si, N., Bian, B., & Ding, J. (2018). The effect of acteoside on puromycin nephropathy and podocyte injury model. Chinese Journal of Nephrology, 30-35. (Year: 2018).*

(Continued)

*Primary Examiner* — Dale R Miller
(74) *Attorney, Agent, or Firm* — Nelson Mullins Riley & Scarborough LLP; Anthony A. Laurentano

(57) ABSTRACT

Provided in the present invention is the use of a verbascoside in the preparation of a drug for preventing or treating glomerular podocyte injured renal disease, belonging to the field of medicine. The inventors found that the verbascoside can effectively restore the viability of glomerular podocytes, reduce the abnormal migration ability thereof, protect the cytoskeletons of the podocytes, and restore the expression levels of podocyte injury markers, i.e. nephrin protein and synaptopodin protein, thereby significantly reducing urinary protein. Therefore, the verbascoside can be applied to prepare drugs or healthcare products for preventing or treating diseases associated with glomerular podocyte injury, alone or in combination with other drugs, and to prepare drugs or healthcare products for alleviating damage to podocytes caused by other drugs, thereby providing new treatment means and ideas for diseases caused by glomerular podocyte injury.

13 Claims, 3 Drawing Sheets

(56) References Cited

OTHER PUBLICATIONS

Chinese Search Report, CN201710783928.5, dated Feb. 18, 2019, 1 page.
Chinese First Office Action, CN201710783928.5, dated Feb. 21, 2019, 5 pages.
International Search Report, PCT/CN2017/106171, dated Jun. 7, 2018, 4 pages.

* cited by examiner

USE OF VERBASCOSIDE IN PREPARATION OF DRUG FOR PREVENTING OR TREATING GLOMERULAR PODOCYTE INJURED RENAL DISEASE

CROSS-REFERENCE TO RELATED APPLICATIONS

This application is a 35 U.S.C.§ 371 national stage filing of PCT Application No. PCT/CN2017/106171, filed on Oct. 13, 2017 and entitled "Use of Verbascoside in Preparation of Drug for Preventing or Treating Glomerular Podocyte Injured Renal Disease", which claims priority to Chinese patent application number 201710783928.5 filed with the Chinese patent office on Sep. 4, 2017, and entitled "Use of Verbascoside in Preparation of Drug for Preventing or Treating Glomerular Podocyte Injured Renal Disease", which is incorporated herein by reference in its entirety.

TECHNICAL FIELD

The present disclosure relates to the field of medicine, in particular to use of verbascoside in preparation of a drug for preventing or treating glomerular podocyte injured renal disease.

BACKGROUND ART

Proteinuria is an important clinical symptom of renal diseases, and is also an independent dangerous factor when such diseases develop to an end stage. Reducing and controlling occurrence of proteinuria can delay the progress of renal diseases, therefore, looking for a safe and effective proteinuria treating target is a key point and a hot point of researches currently in the kidney field.

In recent years, more and more researches prove that podocyte damage is a core factor causing the occurrence of proteinuria, and structural and functional abnormalities of the podocytes can cause structural and functional abnormalities of slit diaphragm, disappearance of foot process, glomerular filtration dysfunction, and entry of macromolecular proteins into urine, so as to form proteinuria. That is to say, the renal diseases are usually accompanied by damage to the glomerular podocytes. Therefore, a drug's effect on podocyte damage determines its therapeutic effect on renal diseases. In view of this, the present disclosure proposes a new solution for treating proteinuria.

SUMMARY

An object of the present disclosure lies in providing new use of verbascoside, providing new treatment means and thought to diseases caused by glomerular podocyte damage.

In order to realize the above object of the present disclosure, following technical solutions are particularly adopted:

Use of verbascoside in preparation of a drug or a health care product for preventing or treating glomerular podocyte damage.

Use of verbascoside in preparation of a drug or a health care product for restoring expression level of nephrin in glomerular podocyte.

Use of verbascoside in preparation of a drug or a health care product for restoring gene expression level of nephrin in glomerular podocyte.

Use of verbascoside in preparation of a drug or a health care product for restoring expression of synaptopodin in glomerular podocyte.

Use of verbascoside in preparation of a drug or a health care product for restoring gene expression of synaptopodin in glomerular podocyte.

Use of verbascoside in preparation of a drug or a health care product for preventing or treating a glomerular podocyte injured renal disease.

Use of verbascoside in preparation of a drug or a health care product for relieving podocyte damage from a drug.

Use of verbascoside in combination with a kidney treatment drug in preparation of a drug or a health care product for preventing or treating podocyte damage.

Compared with the prior art, beneficial effects of the present disclosure, for example, include:

The glomerular podocyte disease, as a clinically common renal disease, includes membranous nephropathy, minimal pathological nephropathy, focal segmental glomerulosclerosis, diabetic nephropathy, lupus nephropathy, membrane proliferative lesions and so on, and currently, effective treatment is clinically lacked. The functionally structural change of podocytes of glomerulus is an important factor of generating a large amount of proteinuria in these diseases above, and intervening in this link is one of the approaches to treat these glomerular injured renal diseases.

Researches of the inventor found that verbascoside can effectively restore activity of the glomerular podocyte, lower its abnormal migration capability, protect cytoskeleton of the podocyte, and restore expression levels of podocyte damage markers, nephrin protein and synaptopodin protein, so as to remarkably reduce the urine protein. Therefore, the verbascoside can be applied, alone or in combination with other drugs, to prepare a drug or a health care product for preventing or treating diseases related to glomerular podocyte damage, and applied in a drug or a health care product for relieving damage to podocyte caused by other drugs.

BRIEF DESCRIPTION OF DRAWINGS

In order to more clearly illustrate technical solutions in the embodiments of the present disclosure or in the prior art, accompanying drawings that need to be used in the description of the embodiments or the prior art will be introduced briefly below.

DETAILED DESCRIPTION OF EMBODIMENTS

Figure 1:
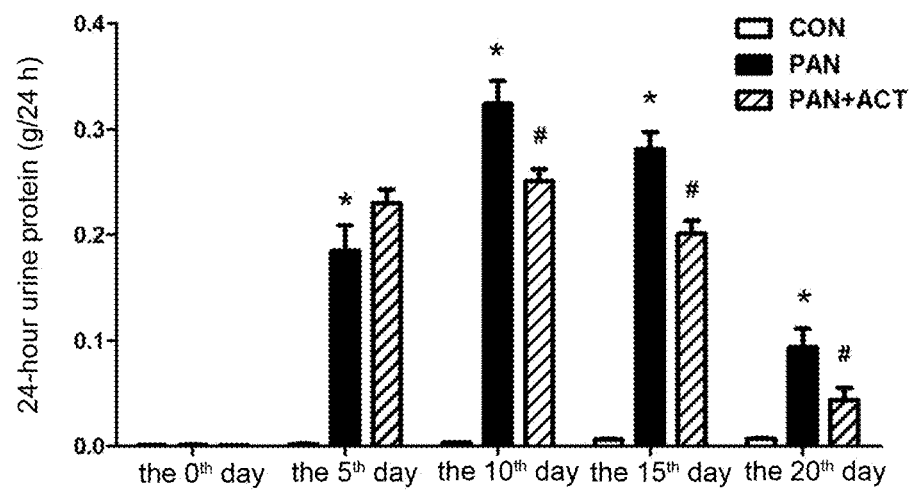
FIG. 1 shows the effect of verbascoside on proteinuria of rats suffering from puromycin-caused nephropathy in Example 1 (CON: normal control group, PAN: puromycin disease group, PAN+ACT: puromycin+verbascoside group. *: $p<0.05$ vs CON, #: $p<0.05$ vs PAN, n=5-8)

Embodiments of the present disclosure will be described in detail below in combination with examples, while a person skilled in the art would understand that the following examples are merely used for illustrating the present disclosure, but should not be considered as limitation on the scope of the present disclosure. If no specific conditions are specified in the examples, they are carried out under normal conditions or conditions recommended by manufacturers. If manufacturers of reagents or apparatuses used are not specified, they are conventional products commercially available.

Proteinuria is an important clinical symptom of renal diseases, therefore, looking for a safe and effective proteinuria treating target is a key point and a hot point of researches currently in the kidney field. In recent years, many researches show that podocyte damage is a core factor causing occurrence of proteinuria, and structural and functional abnormalities of podocytes can cause structural and functional abnormalities of slit diaphragm, disappearance of foot process, glomerular filtration dysfunction, and entry of macromolecular proteins into urine, so as to form proteinuria. This indicates that the renal diseases are usually accompanied by damage to the glomerular podocytes.

The glomerular podocyte disease is a clinically common renal disease. The functionally structural change of podocytes of glomerulus is an important factor of generating a large amount of proteinuria in these diseases above, and thus intervening in this link is one of the approaches to treat these glomerular injured renal diseases.

In view of this, the present embodiment provides a new approach to treat or prevent glomerular podocyte damage, namely, new use of verbascoside, specifically as follows:

Acteoside (hereinafter abbreviated as ACT), also known as mullein glucoside, and called as Verbascoside or Kusaginin in English, has the molecular weight of 624.59, the molecular formula of $C_{29}H_{36}O_{15}$, and CAS No.: 61276-17-3. A structural formula thereof is as follows:

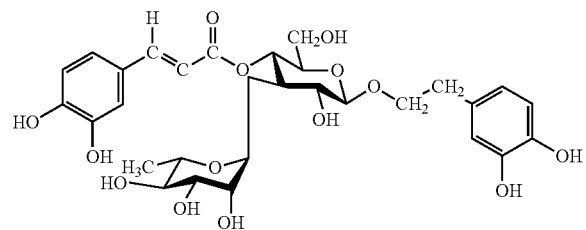

Verbascoside is a phenylethanoid glycoside compound, existing in a plurality of angiosperms such as rehmanniae leaf, herba cistanchis, and folium Callicarpae Formosanae. Now, pharmacological researches prove that such ingredient has wide pharmacological effects such as immunoregulation, neuroprotection, liver protection, kidney tonification and yang strengthening, anti-inflammation, and platelet aggregation resistance.

Researches prove that verbascoside, basically nontoxic, is a safe and effective natural active ingredient, and can be used in various clinical medicines for oral administration, injection administration, mucosa administration, etc. At the same time, this ingredient is extremely water-soluble, and preparation thereof is suitable for any pharmaceutically acceptable dosage form.

In one aspect, the present embodiment provides use of verbascoside in preparation of a drug or a health care product for preventing or treating glomerular podocyte damage.

Researches of the inventor found that verbascoside can effectively restore podocyte activity, lower its abnormal migration capability, and protect cytoskeleton of the podocyte, so as to remarkably reduce urine protein. Therefore, it is indicated that the verbascoside has the efficacy of preventing or treating glomerular podocyte damage.

Further, researches proved that when the podocyte of glomerulus is damaged, the expression levels and the gene expression levels of nephrin protein and synaptopodin protein in the podocyte will both decrease, thereby it is indicated that the nephrin protein and the synaptopodin protein are protein markers of the glomerulus podocyte damage, and are used to indicate whether the glomerular podocyte is damaged or not.

Through in-vitro and in-vivo efficacy researches of the verbascoside, the inventor found that the verbascoside can remarkably improve the protein expression levels of nephrin and synaptopodin in the podocyte damage, and improve the gene expression of nephrin and synaptopodin, so as to protect the podocyte.

In view of this, it is indicated that the verbascoside can be used for preparing a drug or a health care product for restoring the expression level of the nephrin protein in the glomerular podocyte; and the verbascoside can be used for preparing a drug or a health care product for restoring the gene expression level of the nephrin protein in the glomerular podocyte.

Likewise, the verbascoside can be used for preparing a drug or a health care product for restoring expression of synaptopodin protein in the glomerular podocyte; and the verbascoside can be used for preparing a drug or a health care product for restoring the gene expression of synaptopodin protein in the glomerular podocyte.

In another aspect, the present embodiment provides use of verbascoside in preparation of a drug or a health care product for preventing or treating a glomerular podocyte injured renal disease.

Furthermore, the glomerular podocyte injured renal diseases include minimal pathological nephropathy, focal segmental glomerulosclerosis, diabetic nephropathy, lupus nephropathy, membrane proliferative nephropathy, and membranous nephropathy. All of these renal diseases will produce a large amount of proteinuria, and the functionally structural change of podocytes of glomerulus is an important factor of generating a large amount of proteinuria in these renal diseases. Therefore, the verbascoside, having a protective effect on the podocytes of the glomerulus, can be used for treating these renal diseases.

More preferably, the glomerular podocyte injured renal diseases include minimal pathological nephropathy, and focal segmental glomerulosclerosis. Researches of the inventor prove that the verbascoside has better treatment effects on the two renal diseases caused by glomerular podocyte damage, namely, minimal pathological nephropathy and focal segmental glomerulosclerosis, and further can be used for preparing a drug or a health care product for treating the two renal diseases.

In another aspect, the present embodiment provides use of verbascoside in preparation of a drug or a health care product for relieving podocyte damage from a drug.

Since kidney masters excretion, and play a great role in both metabolism and excretion of food or drugs, they are relatively vulnerable to damage from exogenous drugs. In practice, it has been found that certain exogenous drugs, after being used, can lower the expression levels of nephrin and synaptopodin, and damage the glomerular podocytes. Upon researches, the inventor found that the verbascoside can protect the podocytes, and relieve the podocyte damage from such exogenous drugs. Therefore, the verbascoside can be used for preparing a drug or a health care product for relieving podocyte damage from a drug.

In another aspect, the present embodiment provides use of verbascoside in combination with a kidney treatment drug in preparation a drug or a health care product for preventing or treating podocyte damage.

Furthermore, the verbascoside can be used, as an active ingredient, together with a pharmaceutically acceptable auxiliary material or carrier, to prepare a pharmaceutical composition, and this pharmaceutical composition can be in a plurality of dosage forms.

In order to enable this pharmaceutical composition to release the active ingredient rapidly and continuously over a long period of time, this pharmaceutical composition can be prepared according to those conventional methods disclosed in the present technical field. An administration route of this pharmaceutical composition is oral administration, nasal inhalation, or parenteral administration. Preparations of this pharmaceutical composition may be powder, granule, tablet, emulsion, syrup, aerosol, soft capsule, hard capsule, sterile injection, sterile powder, etc.

Herein, the term "pharmaceutically acceptable" means that a compound is physiologically acceptable when administrated to human beings, without causing allergic reactions such as gastrointestinal disorders and dizziness, or systemic allergic reactions similar to these allergic reactions.

In the present disclosure, "pharmaceutically acceptable auxiliary material or carrier" includes but is not limited to: binder (e.g., microcrystalline cellulose, alginate, gelatin and polyvinylpyrrolidone), filler (e.g., starch, sucrose, glucose and anhydrous lactic acid), disintegrant (e.g., crosslinked PVP, crosslinked sodium carboxymethyl starch, crosslinked sodium carboxymethyl cellulose, and low-substituted hydroxypropyl cellulose), lubricant (magnesium stearate, aluminum stearate, talc, polyethylene glycol, sodium benzoate), wetting agent (e.g., glycerin), surfactant (e.g., cetyl alcohol) and absorption enhancer, flavor, sweetener, diluent, coating agent and so on.

The features and performances of the present disclosure are further described below in detail in combination with examples.

Examples

The therapeutic effect of verbascoside provided in embodiments of the present disclosure on podocyte damage is evaluated below in combination with experimental data.

I. Experiment Process:

1. Establishment of Model of Rat Suffering from Puromycin-Caused Nephropathy

The animal experiment was approved by Animal Ethics Committee of Peking University First Hospital, with Resolution No.: J201644. 51 male Sprague-Dawley rats (6 weeks) of the same batch were purchased from Beijing Charles River Company, raised at the animal center of Peking University First Hospital (clean grade), and randomly divided into 3 groups after 3 days of acclimation:

1. normal control group (CON)
2. puromycin disease group (PAN)
3. puromycin+verbascoside-treated group (PAN+ACT)

In the above, groups 2 and 3 were intraperitoneally subjected to single injection of puromycin (Sigma P7130) by 15 mg/100 g at day 0 of the experiment. The normal control group was intraperitoneally injected with the same dosage of physiological saline. Group 3 was intragastrically treated with 10 mg/kg verbascoside every day, and groups 1 and 2 were intragastrically treated with the same dosage of injection water every day. In the experiment process, 24-hour urine of the rats was collected respectively before the administration (Day 0), and at the $5^{th}$ day, the $10^{th}$ day, the $15^{th}$ day, and the $20^{th}$ day (Day 5, Day 10, Day 15, and Day 20) after the administration, for quantitative measurement of urine protein (Hitachi 7170A full-automatic biochemical analyzer). The rats were sacrificed at the $20^{th}$ day (Day 20) after the injection of puromycin, and kidney specimens were collected, which were subsequently used for extracting protein, extracting RNA, taking paraffin-embedded and frozen specimens, and separating glomeruli.

2. Cell Culture

A mouse podocyte line MPC5 was offered by professor Peter Mundel from Mount Sinai Medical School, New York, USA. After recovery, podocytes were placed in a 33° C., 5% $CO_2$ cell incubator to be cultured for proliferation thereof. When a fusion degree thereof reached about 80%, the podocytes were transferred into a 37° C. incubator to be differentiated for 10-14 days such that the podocytes were differentiated to be mature. After the podocytes were differentiated to be mature, the podocytes were inoculated in a 6-well plate, and after the podocytes adhered to the wall, puromycin and verbascoside were added into the plate to stimulate the podocytes for 24 hours, and then proteins or RNAs were collected for later detection.

3. Western Blot

To the separated glomeruli or cells, a corresponding dosage of protein lysate RIPA (50 Mm Tris.cl (pH 7.4), 150 Mm NaCl, 0.1% SDS, 1% Triton-100, 10 Mm EDTA, 1% sodium deoxycholate and protease inhibitor (Roche P8340) was added, and after lysis, proteins were extracted for later detection. An electrophoresis and immunoreaction process was as follows: after separation gel and spacer gel were prepared, samples were loaded and electrophoresis started, wherein the electrophoresis was carried out at a voltage of 80 V for 20-30 minutes, 120 V for about 90 minutes, followed by performing transmembrane at a constant voltage of 300 milliamperes for 100 minutes, and staining with ponceau, the protein separation state was preliminarily observed, and target protein bands were cut according to different molecular weights, and placed in 5% milk prepared with PBST to be blocked for 30-60 minutes, then specific primary antibodies were added, for incubation at 4° C. overnight (12-16 h), wherein the primary antibodies involved in the present research were: nephrin (Sigma, PRS2265-100UG), and β-actin (Santa, sc-130656), and after washing with PBST for 10 minutes 3 times the next day, corresponding secondary antibodies (Sungene Goat anti-rabbit IgG (H+L)-HRP LK2001, Goat anti-mouse IgG (H+L)-HRP LK2003) were added, at room temperature for 1-1.5 hours, and finally, after washing with PBST for 10 minutes 3 times, color development and exposure were carried out.

4. RNA Extraction and Real-time Quantitative PCR

To the collected glomeruli or cells, Trizol (Thermo 15596026) was added, after fully mixing, they were placed on ice for 5 minutes, then chloroform (Beijing Chemical Works) was added, after centrifugation, an upper layer water phase was transferred into a new EP tube, isopropanol (Beijing Chemical Works) with the same volume was added for precipitation, followed by centrifugation to remove supernatant, 75% ethanol with a volume 2 times the precipitate was added for washing, then the resultant mixture was subjected to centrifugation to remove supernatant, and precipitated and dried for 5-10 minutes, wherein 15 μl of DEPC water (Amresco E476-100ML) was added into the dried precipitate to measure purity and concentration, and then stored at −80° C. or directly reversely transcribed to cDNA (TransGen AT301-02). After RNA was reversely transcribed to cDNA, real-time quantitative PCR reaction (TransGen AQ401-01) was carried out, cDNA synthesized by the above reverse transcription was taken as a template, to establish 20 μl of qPCR reaction system. After the reaction system was prepared with 0.5 μl of Forward Primer (10 Mm), 0.5 μl of Reverse Primer (10 Mm), 12.5 μl of 2×qPCR SuperMix, 2 μl of cDNA template, and ddH$_2$O to 20 μl, detection was made on a machine (a real-time quantitative PCR machine was CFX real time PCR instrument of Bio-Rad company, USA, and reaction condition were as follows: 50° C. for 2 minutes, 95° C. for 10 minutes, (95° C. for 5 s, 61° C. for 31 s) for 35 cycles. Sequences of the primers used are as follows:

```
β-actin:
sense: 5-AGCCATGTACGTAGCCATCC-3
antisense: 5-GCTGTGGTGGTGAAGCTGTA-3

NPHS1:
sense: 5-ATGCTGACCCATCCCTGTC-3
antisense: 5-CCACCACACAGGTTGGATTT-3.
```

5. Detection of Podocyte Activity with MTS

After subculturing and counting the podocytes, the podocytes were uniformly inoculated into a 96-well plate at a density of $1.0 \times 10^5$/mL, after the cells adhered to the wall, puromycin and verbascoside were respectively added to treat the podocytes, then after 24 h, the culture medium was discarded, a culture medium containing MTS (Promega G1112) was added with the MTS content of 10 μl MTS per 100 μl of the culture medium, the 96-well plate added with the MTS was placed in a light-tight environment at 37° C. for 4 h and then taken out, and an OD value was measured at 490 nm wavelength using the ELIASA.

6. Cell Migration Experiment

The differentiated podocytes were inoculated on a 6-well plate coated with rat type I collagen, and when the fusion degree thereof reached 60%, a line was scratched on a baseboard using a 200 μL sterile high-pressure gun tip, then the plate was flushed clean using PBS and a clean culture medium was used in replacement, which time was served as the $0^{th}$ hour, and a photo was taken by an inverted microscope, then a corresponding drug was added for intervention, then after 24 hours, a photo was taken again, and finally analysis was made using ImageJ software. The final result was expressed by percentage of coverage.

7 Immunofluorescence

The kidney tissue was sliced. First, slices were subjected to xylene and gradient alcohol deparaffinization, followed by antigen retrieval, and then punched with 0.3% Triton-PBS. After washed with PBS, the slices were blocked with 5% BSA, then the specific primary antibodies were added, and the mixture stayed in a wet box at 4° C. overnight, on the next day, the mixture was washed with PBS, fluorescent secondary antibodies were added in a light-tight condition at room temperature for 30 minutes (in the wet box), then a nuclear dye DAPI (ZSGB-BIO) 1:500 was used for incubation at room temperature for 30 minutes (in the wet box). The mixture was rinsed with deionized water, mounted with 50% buffered glycerol, edge sealed with nail polish, observed under a fluorescence microscope, and photographed. In the cell experiment, the cells were first inoculated in the 6-well plate, then fixed with 4% paraformaldehyde (cells) (Legene DF0135) at room temperature for 15 minutes, then washed with PBS, and then punched with 0.3% Triton-PBS, followed by the same steps as those for the tissue slices.

8. Statistical Analysis

Each experiment was repeated three times, and data were processed using GraphPad Prism statistical software, version 5 (San Diego, Calif., USA). One-way analysis of variance (one-way ANOVA) was used for comparison among multiple groups, and independent sample T-test was used for comparison between two groups, and $P<0.05$ means that the difference was statistically significant.

II. Test Results:

1. Effect of Verbascoside on Proteinuria of Rats Suffering from Puromycin-Caused Nephropathy In order to determine the therapeutic effect of verbascoside on the rats suffering from puromycin-caused nephropathy, the rats were divided into 3 groups, normal control group (CON), disease group (PAN), and verbascoside group (PAN+ACT). 24-hour urine of the rats in each group were sampled every 5 days. The effect of verbascoside for treating the nephropathic proteinuria level was reflected by collecting and detecting blood and urine samples of the rats in each group.

Results of laboratory examination are as shown in FIG. 1. In the disease group, i.e., in the models of rat suffering from puromycin-induced nephropathy, 24-hour urine protein was significantly higher than that of the normal control group on the $5^{th}$ day, reached a peak value on the $10^{th}$ day, and then began to fall down slowly. On the $20^{th}$ day, the proteinuria decreased significantly but was still higher than that of the normal control group. In the treated group, on the $5^{th}$ day, the 24-hour urine protein of the verbascoside group was not significantly different from that of the puromycin group, but on the $10^{th}$ day, the 24-hour urine protein of the verbascoside group decreased significantly compared with that of the disease group, indicating that the verbascoside could relieve the progress of the puromycin-induced proteinuria of rats, and meanwhile, the 24-hour proteinuria results on the $15^{th}$ day and the $20^{th}$ day showed that the abnormality of proteinuria of nephropathic rats could be remarkably relieved in the verbascoside-treated group. 2. Protective Effect of Verbascoside on Podocytes of Rats Suffering from Puromycin-Caused Nephropathy A most typical pathological change of the models of rat suffering from puromycin-induced nephropathy is the fusion and disappearance of podocyte foot process under an electron microscope. This abnormal change of podocytes leads to the development of proteinuria and disease, and also indicates that the podocyte abnormality is an important factor for the occurrence and development of proteinuria and renal diseases. Therefore, in the present research, in addition to detecting the 24-hour proteinuria, whether the verbascoside could protect the podocytes against damage was also verified.

Figure 2:
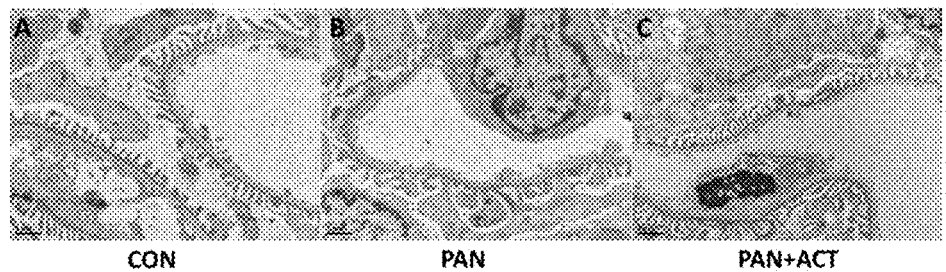
FIG. 2 shows the protective effect of verbascoside on podocyte foot process in Example 1 (CON: normal control group, PAN: puromycin disease group, PAN+ACT: puromycin+verbascoside-treated group. Black bar: 1 μm.)

As shown in FIG. 2, at the end point of the experiment of the puromycin-induced nephropathic models, i.e. on the $20^{th}$ day of the puromycin-induced nephropathic models, partial foot process fusion occurred to the podocytes in the puromycin group, indicating abnormal foot process (A and B of FIG. 2), and in the verbascoside group, the podocyte foot process recovered apparently, and fused occasionally, and is similar to the normal control group (C of FIG. 2), indicating that the verbascoside could restore the condition of abnormal fusion of the podocyte foot process.

In addition to pathological change, in order to determine the protective effect of the verbascoside on the podocytes in the nephropathic rat models, markers of podocyte damage, synaptopodin and nephrin, were also detected in the present research.

Figure 3:
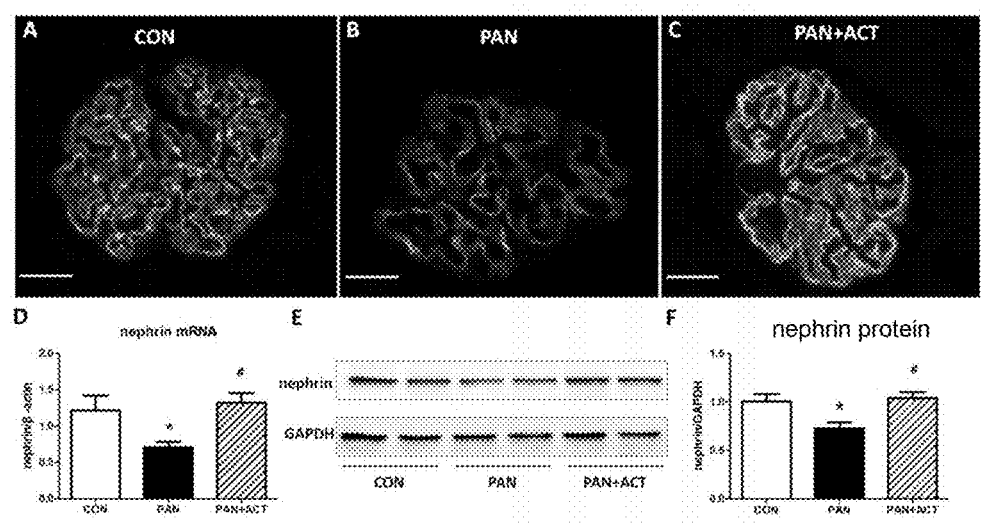
FIG. 3 shows the effect of verbascoside on podocyte damage markers in Example 1: (CON: normal control group, PAN: puromycin disease group, PAN+ACT: puromycin+verbascoside-treated group. *: $p<0.05$ vs CON, #: $p<0.05$ vs PAN, n=5-8, White bar: 40 μm.)

As shown in A-C of FIG. 3, on the 20$^{th}$ day of the experiment, the podocyte damage marker, synaptopodin was stained by means of immunofluorescence, and the protective effect of the verbascoside on the podocytes was detected according to the fluorescence intensity. The puromycin group has weaker fluorescence intensity than the normal control group, that is, having less synaptopodin expression, indicating podocyte damage; in the verbascoside group, the fluorescence intensity was recovered, indicating that the verbascoside could protect the podocytes by improving the synaptopodin expression.

In addition, on the 20$^{th}$ day of the experiment, the nephrin gene and protein expression levels were detected by western and real-time quantitative PCR techniques (D-F of FIG. 3). Results show that gene and protein levels of nephrin both decreased in the puromycin disease group, indicating the podocyte damage; and the expression level of nephrin was increased after treatment with the verbascoside, indicating that the verbascoside could protect the podocytes.

3. Protective Effect of Verbascoside on Podocytes in In Vitro Research

Results of in vivo research of the nephropathic animal models indicate that the verbascoside could protect the podocyte and further reduce the proteinuria, and in order to further confirm the protective effect of the verbascoside on the podocytes, the effect of the verbascoside was further verified in the present research using a cell model with puromycin-induced podocyte damage. First, an in vitro puromycin-induced podocyte damage model was established in the present research.

Figure 4:
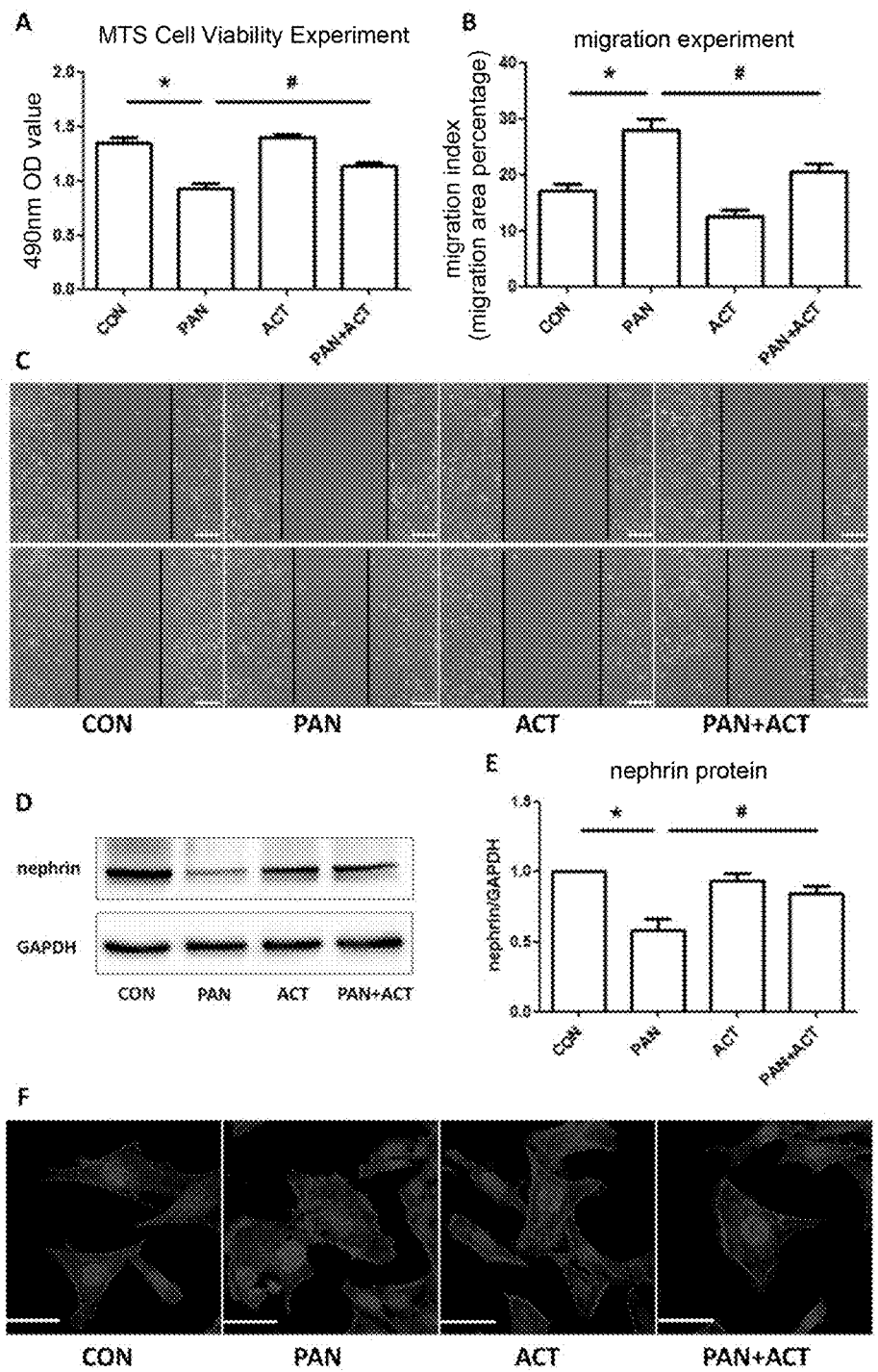
FIG. 4 shows that verbascoside protects podocyte against puromycin-induced podocyte damage (CON: normal control group, PAN: puromycin disease group, ACT: verbascoside group, PAN+ACT: puromycin+verbascoside-treated group. *: $p<0.05$ vs CON, #: $p<0.05$ vs PAN, n=3. White bar in C: 200 μm, White bar in F: 40 μm).

As shown in A of FIG. 4, in the cell viability experiment, MTS (MTS is a formazan compound, dehydrogenase enzymes in live cells convert MTS to a liquid and soluble formazan compound, the number of formazan products represented by an absorption value measured at 490 nm is directly proportional to the number of active cells in the culture, and MTS is therefore used to detect cell viability) detected that when the podocytes were treated with puromycin, the podocyte viability decreased, and was statistically different from the control group. When the verbascoside was used for the puromycin-induced podocyte damage, the podocyte viability was recovered, and statistically different from the damage group.

Thirdly, migration experiment of the podocytes was also used to verify that the verbascoside could protect the podocytes, and some researches have reported that the podocytes have certain mobility under a normal physiological condition, and when the podocytes are damaged, the podocyte migration capability is enhanced. In the test, before treated with the puromycin, the podocytes were scratched with a sterile yellow gun tip (0 hour) and then imaged, after 24 hours, the scratch was subjected to image acquisition and analysis again. Results show that under the treatment with puromycin, as shown in B and C of FIG. 4, after the podocytes were treated with puromycin, an area occupied by cell migration increased, indicating enhancement of the dynamic migration capability of the podocytes, and the intracellular cytoskeleton became unstable due to damage, indicating podocyte damage. The podocyte migration capability was restored after the treatment with the verbascoside, indicating that the verbascoside could restore abnormal migration capability of the podocytes.

Meanwhile, the expression of the protein marker nephrin of the podocyte damage in the puromycin-induced podocyte damage was lowered, indicating podocyte damage. The nephrin expression was improved after the treatment with verbascoside, and the protein improvement was statistically different compared with that of the puromycin group (D and E of FIG. 4).

In addition, podocyte cytoskeletal microfilamentous proteins were stained with phalloidin, and results showed that microfilamentous protein fiber bundles of cytoskeleton in the normal podocytes were also arranged in order in a certain stress direction, and that when the podocytes were damaged, the cytoskeletal microfilamentous proteins were in short-rod-like disordered arrangement, as shown in F of FIG. 4, in which the cytoskeletons of the podocytes are in short-rod-like disordered arrangement after being treated with puromycin; but after the verbascoside was used, the arrangement of the cytoskeletons was restored, and the arrangement was relatively neat, indicating that the verbascoside could protect the podocytes against damage.

To sum up, the present disclosure discloses that the verbascoside can effectively restore the activity of the glomerular podocyte, lower its abnormal migration capability, protect the cytoskeleton of the podocyte, and restore the expression levels of podocyte damage markers, nephrin protein and synaptopodin protein, so as to remarkably reduce the urine protein. Therefore, the verbascoside can be applied, alone or in combination with other drugs, to prepare a drug or a health care product for preventing or treating diseases related to glomerular podocyte damage, and applied in use of a drug or a health care product for relieving damage to podocyte caused by other drugs.

Although the present disclosure has been illustrated and described with specific embodiments, it should be aware that many other alterations and modifications can be made without departing from the spirit and scope of the present disclosure. Therefore, it means that the attached claims cover all these changes and modifications within the scope of the present disclosure.

What is claimed is:

1. A method of improving an expression level of nephrin protein and/or synaptopodin protein in glomerular podocyte, comprising administering an effective amount of a pharmaceutical composition to a subject having a renal disease, wherein the pharmaceutical composition comprises verbascoside.

2. A method of improving an expression level of nephrin protein and/or synaptopodin protein in glomerular podocyte, comprising administering an effective amount of a pharmaceutical composition to a subject having a renal disease, wherein the pharmaceutical composition comprises verbascoside and a kidney treatment drug.

3. The method according to claim 1, wherein the expression level is for nephrin protein or synaptopodin protein.

4. The method according to claim 1, wherein the pharmaceutical composition comprises a pharmaceutically acceptable auxiliary material or carrier.

5. The method according to claim 4, wherein the pharmaceutically acceptable auxiliary material or carrier is one or more selected from the group consisting of a binder, a filler, a disintegrant, a lubricant, a wetting agent, a surfactant, an absorption enhancer, a flavor, a sweetener, a diluent and a coating agent.

6. The method according to claim 5, wherein the binder is at least one selected from the group consisting of microcrystalline cellulose, alginate, gelatin and polyvinylpyrrolidone.

7. The method according to claim 5, wherein the filler is at least one selected from the group consisting of starch, sucrose, glucose and anhydrous lactic acid.

8. The method according to claim 5, wherein the disintegrant is at least one selected from the group consisting of crosslinked PVP, crosslinked sodium carboxymethyl starch, crosslinked sodium carboxymethyl cellulose and low-substituted hydroxypropyl cellulose.

9. The method according to claim 5, wherein the lubricant is at least one selected from the group consisting of magnesium stearate, aluminum stearate, talc, polyethylene glycol and sodium benzoate.

10. The method according to claim 5, wherein the wetting agent is glycerin.

11. The method according to claim 5, wherein the surfactant is cetyl alcohol.

12. The method according to claim 1, wherein a dosage form of a preparation of the pharmaceutical composition is selected from the group consisting of powder, granule, tablet, emulsion, syrup, aerosol, soft capsule, hard capsule, sterile injection and sterile powder.

13. The method according to claim 1, wherein an administration route of the pharmaceutical composition is selected from the group consisting of oral administration, injection administration, nasal inhalation and parenteral administration.

* * * * *